United States Patent [19]
Arpaia et al.

[11] Patent Number: 5,128,453
[45] Date of Patent: Jul. 7, 1992

[54] URINARY FOLLICLE STIMULATING HORMONE

[75] Inventors: Guiseppe Arpaia; Serenella Serani; Antonino Sirna; Stefano Villa, all of Rome, Italy

[73] Assignee: Istituto DiRicerca Cesare Serono SpA, Rome, Italy

[21] Appl. No.: 337,766

[22] PCT Filed: Jun. 24, 1988

[86] PCT No.: PCT/IT88/00048
§ 371 Date: Feb. 7, 1989
§ 102(e) Date: Feb. 7, 1989

[87] PCT Pub. No.: WO88/10270
PCT Pub. Date: Dec. 29, 1988

[30] Foreign Application Priority Data
Jun. 26, 1987 [IT] Italy .................................. 48110A/87

[51] Int. Cl.⁵ ........................... C07K 3/18; C07K 3/20; C07K 3/28
[52] U.S. Cl. .................................. 530/398; 530/397; 530/350; 530/413; 530/412; 530/415
[58] Field of Search ............... 530/397, 350, 413, 417, 530/415, 398

[56] References Cited
FOREIGN PATENT DOCUMENTS
WO86/04589 8/1986 PCT Int'l Appl.
2173803 10/1986 United Kingdom.

OTHER PUBLICATIONS
(Abstract, DBA Accession/vo. 87-09420 of Dialog File 357) of Jack et al. 1987, *J. Chem. Technol. Biotech* 39(1):45-58.
(Abstract, accession No. 88140703 of Dialog File 155) of Miller et al. 1987, *J. Endocrinol.* 115(2):382-388.
Chappel et al., Endocrine Reviews 4:179 (1983).
Hallin et al., J. Liq. Chromat. 9:2855 (1986).
Donini et al. (I), Acta, Endocrinologica 52:186 (1966).
Donini et al. (II), Gonadotropins and Ovarian Development (EPS Livingstone) pp. 39-56 (1970).
Donini, The Endocrine Function of the Human Testis (Academic Press) pp. 195-221 (1973).

*Primary Examiner*—Margaret Moskowitz
*Assistant Examiner*—Keith C. Furman
*Attorney, Agent, or Firm*—Stephan P. Williams

[57] ABSTRACT

Purification of human FSH from post-menopausal urine gonadotropin using immunoaffinity chromatography with elution at high pH and reverse-phase HPLC steps yields a biologically active hormone which is free from detectable traces of luteinizing hormone and other urinary proteins.

11 Claims, No Drawings

URINARY FOLLICLE STIMULATING HORMONE

FIELD OF THE INVENTION

This invention relates to urinary follicle stimulating hormone, to pharmaceutical compositions containing it and to a method for its purification.

BACKGROUND OF THE INVENTION

Follicle stimulating hormone (FSH) is known to be useful in the treatment of infertility. Preparations containing this hormone have been employed to assist in effecting pregnancy using both in-vivo and in-vitro techniques. Human FSH has been isolated from human pituitary glands and from post-menopausal urine. More recently, it has been produced using recombinant DNA techniques.

The first commercially available product comprising human FSH contained HMG (e.g., Pergonal® Serono), i.e., human menopausal gonadotropin extracted from post-menopausal urine which is a mixture of FSH, Luteinizing Hormone (LH) and other urinary proteins. Meanwhile, several attempts were made to obtain pure FSH preparations, both for scientific and therapeutic purposes. The product Metrodin® (Serono), currently available in commerce, is a preparation of urinary FSH containing other urinary proteins, but minimum quantities of LH and is used for the treatment of infertility. Use of this product is particularly advantageous when administration of exogenous LH together with FSH is undesirable, e.g., in the polycystic ovary syndrome (PCOS).

So far, administration of FSH for therapeutic purposes has been carried out, successfully, exclusively by intramuscular injection. Since intramuscular injections are generally performed by the physician or by the medical professional staff, the patient is expected to visit a surgery or a hospital regularly in order to receive the treatment. This creates a considerable discomfort. Moreover, the time taken up by this type of application often leads to unsatisfactory compliance by the patient as the treatment normally extends over several weeks or months.

Administration by subcutaneous injection would render possible the self-administration by the patient and consequently improve patient's cooperation and compliance.

The subcutaneous administration of Human Menopausal Gonadotropin (HMG) has already been described (Nakamura Y. et al., Fertility and Sterility, 46(1):46–54, 1986) in connection with the treatment of female infertility by pulsatile administration of HMG via the subcutaneous peristaltic pump. The subcutaneous administration may suffer the drawback of the appearance of local allergies due to the presence of impurities in the product used and, consequently, result in the suspension of the treatment.

P. Roos ("Human Follicle Stimulating Hormone", *Acta Endocrinologica Supplementum* 131, 1968) described and characterized highly purified preparations of pituitary and urinary FSH obtained from frozen pituitaries and from post-menopausal urinary concentrate, respectively. Biological potencies as high as about 14,000 I.U. of FSH activity per mg for pituitary FSH and 780 I.U. of FSH activity per mg for urinary FSH were obtained. The content of LH contamination in the most active pituitary and urinary preparations was estimated to correspond to approximately 0.1 percent by weight. The purification procedures involved one or more of such techniques as chromatography on DEAE-Cellulose, gel-filtration on Sephadex G-100, hydroxylapatite chromatography, polyacrylamide gel electrophoresis, and the like.

One of the best purified urinary FSH preparations was described by Donini et al. ("Purification and partial Chemico-physical characterization of FSH from Menopausal Urine", *Gonadotrophins and Ovarian Development* (Proceedings of two workshop meetings), E and S Livingstone, Edinburgh and London, 1970) and had a biological potency of 1255.6 I.U. FSH per mg with an LH contamination as low as 3.2 I.U. LH per mg. In this case, the starting material was a Human Menopausal Gonadotropin (HMG) preparation (Pergonal®) which, as stated above, is a mixture of FSH and LH hormones and other urinary proteins. This result was achieved by batchwise purification of the starting HMG on DEAE-Cellulose followed by chromatography on a DEAE-Cellulose column, gel filtration on Sephadex G-100 and a final step of preparative polyacrylamide gel electrophoresis.

Even higher biological potencies were achieved by H. Van Hell et al. ("Purification and some properties of human urinary FSH and and LH", *Gonadotropins* (Proceedings of Int.l Symposium on Gonadotropins, 1971), Wiley-Interscience, New York) by adding immunochromatography and gel-filtration steps to a conventional chromatographic purification procedure. Immunochromatography was performed using anti-HCG antibodies coupled to Sepharose for the specific purpose of removing the LH activity from partially purified FSH fractions. The best purified FSH fraction contained 4720 I.U. FSH per mg and the LH contamination was as low as 15 I.U. LH per mg as assayed by RIA.

The immunochromatographic approach had already been described by Donini et al. ("Purification and Separation of FSH and LH from HMG", *Acta Endocrinologica* 52, pages 186-198, 1966) who obtained as early as 1966 an FSH preparation which had a potency of 329.7 I.U. FSH per mg and biologically undetectable amounts of LH contamination. In another experiment, a fraction assaying 148.3 I.U. FSH per mg and 2.4 I.U. LH per mg was obtained. Since no RIA was performed on the 329.7 I.U. FSH per mg preparation, it can be assumed by analogy with the results of H. Van Hell (c.f. supra) that traces of LH would have been found if assayed by RIA.

The physiological relevance of even minimal amounts of LH contamination was shown by Donini et al. in a paper ("A new approach to the Biological Determination of the Luteinizing Hormone", *Acta Endocrinologica*, 58, pages 463-472, 1968) where a new bioassay for LH determination was proposed which consisted in injecting intact immature mice with a constant dose of a biologically pure FSH preparation plus increasing amounts of LH and then measuring the increase in the uterine weight as a response proportional to the LH activity. By this method, as little as 0.068 I.U. of LH were shown to be capable of increasing the uterine weight when injected together with 4.44 I.U. of FSH.

It thus clearly follows that an absolutely pure FSH preparation is desirable when FSH activity in the complete absence of LH activity is requested in therapy.

As mentioned above, the currently marketed product Metrodin ® (Serono) is a purified FSH preparation which is obtained by a method substantially identical to that described by Donini et al. in an already mentioned paper (*Acta Endocrinologica* 52. pages 186-198, 1966). The quality control specifications, in agreement with the declared biological purity of the said preparation, provide for not more than 0.7 I.U. LH per 75 I.U. of FSH, i.e., approximately the sensitivity limit of the biological assay. In certain therapeutic applications, however, the absolute absence of LH is desirable. Furthermore, in Metrodin ®, human FSH is accompanied by substantial amounts of other urinary proteins, i.e., it is not a chemically pure FSH preparation.

U.K. patent application 2,173,803 A provides still another approach to the purification of pituitary glycoprotein hormones, among them FSH. This approach consists of first forming a complex of the hormone with immobilized monoclonal antibodies and then eluting the hormone with an acidic aqueous buffer having a pH from 3 to 4. As far as FSH is concerned, the obtained highly purified hormone is still contaminated with 0.1% by weight of LH and 0.5% by weight of TSH.

Scott C. Chappel et al. describe in a review article (*Endocrine Reviews* 4(2), 179-211, 1983) the microheterogeneity of FSH and the physiological significance of the carbohydrate moieties accompanying the FSH molecule. The hypothesis can be formulated that some modifications occur during the metabolic pathway up to the final urinary secretion which may account for the chemico-physical differentiation demonstrated in the experiments carried out by Applicant between the highly purified urinary FSH preparation (hpuFSH) according to this invention, and the highly purified pituitary FSH preparation used for comparison purposes.

Co- or post-translationally modifications appear to be the basis for microheterogenous diversity of FSH, a glycoprotein consisting of two dissimilar, glycosylated, non covalently linked polypeptide chains known as alpha and beta-subunit. The beta-subunit endows the molecule with its biological specifity.

Incidentally, the same article attempts to explain the substantial difference in the values of biological activity per mg between highly purified pituitary and urinary FSH preparations. A reasonable hypothesis can again be based on the relevance of the carbohydrate moieties and, more specifically, the role of the terminal sialic acid residues.

It should be noted that, while both pituitary FSH and urinary FSH are termed "FSH", no conclusive evidence has yet been found which verifies whether the molecules isolated from the two sources are the same or even chemically equivalent.

DESCRIPTION OF THE INVENTION

It has now been found that human urinary FSH can be isolated from a concentrate of post-menopausal urine to such a degree of purity that the resultant FSH is completely free from any detectable traces of LH and other urinary proteins. Furthermore and contrary to any expectation, the amino acid analysis of the urinary FSH according to the present invention has revealed a novel FSH beta-subunit of 111 amino acids instead of 118 or 108 as reported in the state of the art (see e.g. Scott et al. supra) for the known FSH beta-subunit. More specifically, this invention provides a novel FSH beta-subunit, the amino acid sequence of which is as follows:

```
                                  10
Asn Ser Cys Glu Leu Thr Asn Ile Thr Ile Ala Ile Glu Lys
                        20
Glu Glu Cys Arg Phe Cys Ile Ser Ile Asn Thr Thr Trp Cys
     30                                  40
Ala Gly Tyr Cys Tyr Thr Arg Asp Leu Val Tyr Lys Asp Pro
                        50
Ala Arg Pro Lys Ile Gln Lys Thr Cys Thr Phe Lys Glu Leu
     60                                  70
Val Tyr Glu Thr Val Arg Val Pro Gly Cys Ala His His Ala
                        80
Asp Ser Leu Tyr Thr Tyr Pro Val Ala Thr Gln Cys His Cys
                        90
Gly Lys Cys Asp Ser Asp Ser Thr Asp Cys Thr Val Arg Gly
     100                                 110
Leu Gly Pro Ser Tyr Cys Ser Phe Gly Glu Met Lys Glu
``` as well as a novel protein comprising the known gonadotropin alpha-subunit and the 111 AA beta-subunit as hereabove defined. The protein has follicle stimulating hormone (FSH) biological activity. Preferably it is in glycosylated form. Most preferably it is substantially free from detectable traces of luteinizing hormone and other urinary proteins.

A further aspect of the invention is a pharmaceutical composition containing a purified protein according to the present invention and a pharmaceutically acceptable excipient. Preferably the composition is in a form suitable for subcutaneous administration. It has been found that subcutaneous injection of a pharmaceutical composition according to the present invention does not give rise to the appearance of those allergical reactions normally encountered with the known FSH preparations.

According to a further aspect of this invention, a method is provided to produce the novel and highly purified FSH according to the present application. The method is substantially based on the combination of an immunopurification step with reverse phase HPLC. The immunopurification step uses immobilized monoclonal antibodies substantially as described in the above mentioned U.K. patent application 2,173,803A, but with the fundamental difference that elution of FSH from the immunocomplex is carried out at much higher pH values.

In the process of the present invention elution is conveniently carried out using an aqueous solution having a pH higher than about 10 and a molarity higher than about 0.5. The experiments carried out by Applicant have shown that, in these conditions the immobilized antibody is not substantially inactivated. This is in contrast with the teaching of the above mentioned U.K. patent application which states (on page 1, lines 36-37) that "the use of eluents having such high pHs is not feasible in practice since it leads to rapid inactivation of the antibody".

This difference in behaviour may depend upon differences in the methods adopted to link the antibody to the resin.

According to this invention, the pH of the eluent is preferably higher than 11 and more preferably comprised within the range of 11.3 to 11.7.

Molarity values are preferably higher than 0.8 and more preferably of about 1.

Suitable eluents for use in the invention process are ammonia, diethylamine and such buffers as TRIS buffer, glycine-NaOH and the like.

The subsequent reverse phase high pressure liquid chromatography (HPLC) step permits one to obtain the complete removal of any contaminating proteins. This removal is not achieved by the immuno-purification step alone, as is also acknowledged in the U.K. application text. The fact that such a step not only effectively removes the residual traces of contaminating proteins but also retains all the FSH biological activity is surprising in view of the article by P. Hallin and S. A. Khan (*J. Liq. Chromat.* 9(13), 2855–68, 1986) which shows loss of biological activity for bovine FSH and for human FSH (standard of HMG) when they are subjected to reverse-phase HPLC. On the other hand, the same article shows a satisfactory recovery of biological activity, but only partial separation, when the human urinary preparation (i.e., containing both FSH and LH) is subjected to ion-exchange HPLC.

Following the HPLC step, FSH is recovered using conventional techniques. For storage and/or handling purposes, the product can be lyophilized. Other suitable procedures to effect concentrating, stabilizing or other processing of the product are contemplated.

Clearly, the availability of post-menopausal urine is greater than that of human pituitary glands. This relative availability lends dramatic importance to Applicant's discovery.

The FSH-specific monoclonal antibody for use in the process of this invention may be produced using known techniques.

In a typical example, hybridoma cell line 9/14 was screened for optimal affinity towards FSH at the University of Cambridge. Monoclonal antibodies were produced in supernatant medium by cell culture techniques and purified by means of salt fractionation using 50% (w/v) ammonium sulphate followed by ionic reverse-phase chromatography and HPLC gel filtration and dialysis.

The monoclonal antibody produced by cell line 9/14 and purified as described above had the following specifications:
a) protein purity: not less than 90%
b) class of immunoglobulin: IgG 1
c) affinity constant: $3.5 \times 10^8$ L.mole$^{-1}$
d) specificity:

| Antigen | % cross reaction |
|---|---|
| FSH | 100 |
| HCG | 1 |
| HCG-beta subunit | 1 |
| LH | 1 |
| TSH | 1 | e) binding capacity to FSH in solution: about 1,000 I.U. FSH per mg McAb.

FSH-specific monoclonal antibodies are chemically bound to SEPHAROSE 4B by divinylsulphone according to the method described by J. Porath in *Methods in Enzymology* 34, pages 13–30, 1974.

In a typical example, 1 liter of SEPHAROSE 4B was washed on a porous glass filter first with 5 liters of freshly distilled water and then with 5 liters of 1 M sodium carbonate, pH 11. The washed Sepharose was suspended in 1 liter of 1M sodium carbonate (pH 11). 200 ml of divinylsulphone were added dropwise with continuous stirring. The reaction was completed in 70 minutes at room temperature and then stopped by means of the addition of 1N HCl (up to pH 7.0).

The activated resin was suspended in 1 liter of 0.25M sodium bicarbonate (pH 9.0) containing 2 grams of anti-FSH monoclonal antibody to obtain more than 90% binding of the antibody to the activated resin. The immunoresin obtained was stored at 4° C.

The following Example 1 illustrates the two purification steps of the method of this invention as applied to commercial HMG, i.e, the active ingredient in Pergonal ® Serono.

It is understood that while HMG is the preferred starting material in the invention process, the latter is also applicable to less purified materials such as postmenopausal urine concentrates and the like. Good results have been obtained using as starting material a urinary concentrate containing as low as 1 I.U. FSH per mg.

Other aspects and advantages of the invention will become apparent after consideration of the following examples, which are not intended to be limiting.

EXAMPLE 1

Preparation of highly purified urinary FSH (hpuFSH)

1st Step: Immunopurification on anti FSH McAb-DVS-Sepharose

HMG was used as starting material.

Immunoresin anti-FSH Mcab-DVS-Sepharose was equilibrated in 0.1M Tris-HCl, 0.3M NaCl buffer pH=7.5 at 4° C.

The column was loaded with a quantity of IU FSH (RIA) corresponding to 80–90% of its total FSH binding capacity.

The non-retained proteins were eluted with the equilibrating buffer until the $OD_{280}$ of eluate was lower than 0.02.

The absorbed uFSH was eluted from the immunoresin with 1M ammonia solution at 4° C. Ammonia eluates corresponding to about 4 times the immunoresin volume were pooled, the pH was adjusted to 9.0 as soon as possible at 4° C. by adding glacial acetic acid and the solution was ultrafiltered in an Amicon apparatus (membrane C.O. 10,000 Ds) and concentrated to a small volume.

2nd Step: Reverse phase HPLC

The resultant solution, adjusted at pH=5.6, was loaded on a $C_{18}$ reversed phase column (Prepak 500 $C_{18}$ cartridges Waters) which had previously been equilibrated with 0.05M ammonium acetate pH=5.6 buffer at room temperature.

Flow rate was 100 ml/min and the eluate was monitored at 280 nm.

The HPLC purification was carried out employing a Waters Prep LC 500A liquid chromatograph equipped with UV detector and a preparative gradient generator Biologically active highly purified urinary FSH was eluted by a gradient of isopropanol up to 50% of the mobile phase. Fractions were checked by analytical GPC and RIA.

The organic solvent was removed by distillation under vacuum at 40° C. and then the solution was frozen and lyophilized.

EXAMPLE 2

Characterization of the FSH

The highly purified urinary FSH preparation of the present invention was subjected to several chemicophysical, biological and immunological tests in order to achieve its complete characterization. As indicated below, most of the tests were carried out in comparison with a highly purified pituitary FSH preparation obtained according to the procedure described below.

Crude human pituitary extract (HPG), a by-product resulting from extraction of the Human Growth Hormone, was used as starting material.

The procedure consisted of the following steps:

1) Preliminary purification of crude HPG by extraction with 40% ethanol containing 6% ammonium acetate pH 5.6 and precipitation of supernatant with 96% cold ethanol.

2) Further purification of HPG by ion exchange chromatography on DEAE cellulose, using 0.15M sodium acetate pH 7 as eluent, followed by precipitation with 96% cold ethanol.

3) Further purification of. FSH fraction by gel filtration on SEPHADEX G-100, using 0.05M ammonium bicarbonate as buffer.

4) Last step of FSH purification by ion exchange chromatography on SP SEPHADEX C 50. Highly purified pituitary FSH was eluted with 0.1M phosphate buffer pH 6.2 and lyophilized.

The pituitary FSH in-vivo biological specific activity (Steelman-Pohley test; I.U. of 2nd IRP-HMG) was determined to be 4770 I.U. FSH/mg of lyophilized powder using the methodology described below under "Biological Assay".

The characterization tests performed were as follows:

LH contamination

This test was carried out by means of a specific radioimmunoassay for LH using an LH standard calibrated against the 2nd IRP-HMG and $^{125}$I-LH as the tracer, both contained in the LH ter assay kit (code 10204) currently marketed by the company Biodata ®. As antiserum, a sheep anti-HCG antiserum prepared by the Applicant was used having 100% cross-reactivity to LH and less than 0.1% to FSH.

The RIA procedure as per the manufacturer's instructions was followed to obtain as a result no detectable LH contamination in the highly purified urinary FSH preparation prepared in accordance with the Example 1.

The above results were confirmed using a more sensitive assay called DELFIA (dissociation-enhanced lanthanide fluoro immunoassay) marketed by LKB-Pharmacia.

SDS-PAGE

Slab-gel electrophoresis in SDS was performed, under reducing conditions, on 13.5% polyacrylamide gel pH=8.8 according to the procedure described by Laemmli in *Nature*, 227, pages 680–685 (1970).

Staining was performed with Coomassie Brilliant Blue R-250 0.25% in a 25% methanol/75% acetic acid solution.

Both the hpuFSH preparation according to the invention and the highly purified pituitary FSH preparation (hppFSH) obtained as described above were subjected to this test.

In both the uFSH and pFSH preparations the main large band typical of the glycoproteins is found at the same molecular weight of approximately 20,000 Daltons, which is also in accordance with the literature data. Due to the known behaviour of the glycoproteins in SDS-PAGE, this value is a little overestimated.

Size exclusion chromatography

Analyses of both hpuFSH and hppFSH were performed on a TSK G 2000 SW column by Beckman using 0.1M phosphate buffer pH 6.8+0.2M NaCl as the eluent. Flow was 0.7 ml/minute and readings were made at the wavelength of 230 nanometers.

Single main peaks for both uFSH and pFSH exhibit substantially the same retention times (13.37 and 13.55 minutes, respectively).

Isoelectrofocusing

Isoelectrofocusing was carried out on 5% thin-layer polyacrylamide gel (LKB Ampholine, pH range 3.5 to 9.5) fixed in 11.5% (w/v) TCA and 3.5% (w/v) sulphosalicylic acid and stained with a Silver staining BIO-RAD ® Kit.

Both urinary and pituitary FSHs show several bands but completely different patterns; in particular, the main bands of urinary FSH are at a pH range lower than 4.8 whereas pituitary FSH shows the main bands at a higher pH range.

This test demonstrates that urinary and pituitary FSHs are not identical molecules and that the differences reside at least in their carbohydrate moieties, if not in the protein moieties themselves.

Biological assay

The FSH in-vivo biological activity of hpuFSH was tested by the Steelman Pohley method (*Endocrinology* 53, pages 604–616, 1953) using as the reference material an HMG House Standard calibrated against the 2nd International Reference Preparation of HMG for bioassay. This assay is accepted by all major Pharmacopoeias and Health Authorities for the determination of the International Units (I.U.) of FSH biological activity.

The hpuFSH preparation obtained according to the Example above was determined to have a specific activity of 6200 I.U. of FSH per mg of lyophilized powder, i.e., the highest specific activity ever described for an FSH urinary preparation.

Determination of the Amino Acid sequence a) uFSH Subunit Separation

The separation of the uFSH subunits is performed using a Waters HPLC system equipped with an AQUA-PORE RP-300 column, 200×4.6 mm, 7 um, (Applied Biosystems).

The eluents are A=0.1% TFA (Trifluoroacetic acid, HPLC grade, Pierce), B=0.055% TFA in Acetonitrile.

The flow rate is 1 ml/min at 35° C. and the initial condition is 15% B.

The gradient raised 40% B in 20 min.

The UV detector is set at 229 nm.

Usually in analytical runs 20 mcl of a solution 0.5 mg/ml of hpuFSH and 0.5% TFA is injected.

Preincubation in TFA solution is not necessary, same column.

Good resolution is achieved by injecting 0.5 mg of hp human u FSH (batch no. 032) dissolved in A buffer. Fractions are collected manually and dried down using a Speed Vac concentrator. Subunits are dissolved in water, analized by HPLC and stored at −20° C.

The beta subunit is eluted after about 10.5 min as a broad peak, the alpha subunit elutes at 15 min as a sharp peak.

The recognition of each peak as beta and alpha subunit respectively is accomplished by a specific RIA.

Usually the recovery of the beta subunit is around 50%, the alpha subunit recovery on the contrary is more than 90%.

b) Reduction and Carboxymethylation of the alpha and beta Subunits.

Reduction of the subunits, separated as described in point a), is performed in 0.5 Tris, 0.1% EDTA, 6M Guanidine HCl pH 8.5 for 2 h at 37° C. using DTT (dithiothreitol, Serva) in 15 fold molar excess over cystein content. Sodium iodoacetate (2.1 molar over DTT) is then added to the reaction mixture and left lying for 30 min in the dark.

To stop the reaction 1% mercaptoethanol and TFA is added.

The carboxymethylated subunits are purified by HPLC. The beta carboxymethylated subunit is poorly soluble in water so that the final yeld is quite low.

c) Reduction, pyridylethylation and trypsin digestion of the beta subunit

Reduction of the beta subunit, separated as described in point a) was performed at room temperature for 2 hrs in the following way: 0.1 mg of beta subunit 0.5 ml of 0.5M Tris, 0.1% EDTA, 6M guanidine HCl pH 8.5 2.7 mg Dithiothreitol The Pyridylethylation was performed adding 0.02 ml of 4 vinylpyridine to the previous solution. The reaction takes 2 hrs at room temperature. Finally, the reaction mixture was loaded onto a BAKERBOND C4 Cartridge (Baker) equilibrated with 0.1% TFA. The cartridge was washed with 0.1% TFA and the beta subunit pyridylethylated was eluted with 40% Acetonitrile, 0.1% TFA. The eluted fraction was dried down and purified by HPLC as previously reported for the beta subunit. The pyridylethylated beta subunit previously purified by HPLC was dissolved in 1% $NH_4HCO_3$, pH 8.

The trypsin was added to the solution and the reaction was carried out for 1.5 hrs at 37° C. The tryptic fractions were purified by HPLC using the same procedure previously described, except for the gradient from 0% to 55% in 30' and the UV detector, set at 214 nm.

The tryptic fractions were sequenced in the same way reported for the sequencing of the subunits (cf. point e)).

d) Sequencing of the alpha subunit

Several sequencing runs are performed using alpha subunit, carboxymethylated alpha subunit, or integral highly purified human uFSH usually loading 5 nmoles or less into the protein sequencer (470 A, Applied Biosystem) and using the standard 03RPTH program delivered by Applied Biosystem or a special program where cycles which cleave a Pro or a Gly are substituted by the special cycle 03CPRO. The first 45 residues starting from $NH_2$ terminal of the molecule were identified and the results confirm the amino acid sequence known from the literature (J. Biol. Chem. 250, 6735 (1975). The Asn at position 52 and at position 78 referring to the known sequence starting with Ala are the amino acids where glycosylation occurs. At the $NH_2$ terminal is always present an heterogeneity and is always the same in all samples sequenced. The complete molecule (i.e. starting with Ala) is present in 65% of the chains, the molecule missing the first two amino acids (i.e. starting with Asp) is present in 5%, the molecule missing the first three amino acids (i.e. starting with Val) is present in 30%.

|  | 1 |  |  |  | 5 |
|---|---|---|---|---|---|
| 65% of chains | Ala | Pro | Asp | Val | Gln ... |
| 5% of chains |  |  | Asp | Val | Gln ... |
| 30% of chains |  |  |  | Val | Gln ... |
| Heterogeneity of alpha subunit. |  |  |  |  |  | e) Sequencing of the beta subunit

Several sequencing runs were performed using beta subunit, carboxymethylated beta subunits, integral highly purified human u-FSH and tryptic peptides from pyridylethylated beta subunit.

The samples were loaded into the protein sequencer (470 A, Applied Biosystem) using the standard 03RPTH program delivered by Applied Biosystem. The results show that that beta-subunit is 111 amino acids long and has the following amino acid sequence:

```
                                         10
Asn Ser Cys Glu Leu Thr Asn Ile Thr Ile Ala Ile Glu Lys

20
Glu Glu Cys Arg Phe Cys Ile Ser Ile Asn Thr Thr Trp Cys 30                                   40
Ala Gly Tyr Cys Tyr Thr Arg Asp Leu Val Tyr Lys Asp Pro

50
Ala Arg Pro Lys Ile Gln Lys Thr Cys Thr Phe Lys Glu Leu 60                               70
Val Tyr Glu Thr Val Arg Val Pro Gly Cys Ala His His Ala

80
Asp Ser Leu Tyr Thr Tyr Pro Val Ala Thr Gln Cys His Cys

90
Gly Lys Cys Asp Ser Asp Ser Thr Asp Cys Thr Val Arg Gly 100                              110
Leu Gly Pro Ser Tyr Cys Ser Phe Gly Glu Met Lys Glu
```

The Asn at position 7 and 24 referring to the above sequence starting with Asn at position 1 are the amino acids where glycosilation occurs.

At the $NH_2$ terminal of beta subunit is always present an heterogeneity and is always the same in all samples sequenced. The complete molecule (i.e. starting with Asn) is present in 35% of the chains, the molecule missing the first amino acids (i.e. starting with Ser) is present in 15%, the molecule missing the first two amino acids (i.e. starting with Cys) is present in 50%.

|  | 1 |  |  |  | 5 |
|---|---|---|---|---|---|
| 35% of chains | Asn | Ser | Cys | Gly | Leu ... |
| 15% of chains |  | Ser | Cys | Glu | Leu ... |
| 50% of chains |  |  | Cys | Gly | Leu ... |
| Heterogeneity of beta subunit. |  |  |  |  |  |

EXAMPLE 3

Pharmaceutical preparations

The production of pharmaceutical dosage form preparations containing hpuFSH obtained in accordance with this invention is not particularly difficult. Since the substance maintains its biological activity after lyophilization, this is the preferred form for injectable preparations.

The lyophilized hpuFSH-containing preparation is reconstituted using physiological saline and/or other suitable diluents to yield an injectable solution.

Some excipients may be suitably used in the composition as a part thereof, such as, for example, mannitol, lactose, glycine, glucose, saccharose and their mixtures. Other conventional carriers, fillers and the like can be used. Mixtures are operable.

In the experiments carried out according to the present invention, lactose has been used as the excipient for the injectable preparations.

In preparing injectable formulations, pH is optionally adjusted via the addition of conventional acidic or basic substances. Acidic substances include acetic acid and the like. Basic substances include sodium hydroxide and the like. Mixtures can be employed.

The use of one or more stabilizers, e.g. albumin and the like, is contemplated.

A typical example of pharmaceutical production for the manufacturing of a batch of 20,000 ampoules each containing 75 I.U. FSH is as follows.

The calculated (in units of biological activity) amount of the lyophilized FSH bulk powder is dissolved in 700 ml of cold apyrogenic water for injection. If necessary, pH is readjusted to a value between 6.2 and 6.8 by using either acetic acid or sodium hydroxide, as the case may be. The solution is then sterile filtered through a 0.2 micron pores filter.

200 grams of lactose are dissolved in 2 liters of apyrogenic water for injection, sterile filtered as above and added to the FSH solution.

Apyrogenic water for injection is added to reach a final volume of 15 liters, the solution is dispensed into ampoules (0.75 ml each) and lyophilized in a sterile lyophilizator.

Ampoules are obtained which contain each 75 I.U. FSH and 10 mg lactose.

In a preferred embodiment the ampoules may contain 150 I.U. FSH.

According to a further example of pharmaceutical preparation, ampoules have been prepared which also contain 1 mg of human albumin as stabilizer in addition to the excipient lactose.

Although this invention has been illustrated with specific examples, it is understood that variations may be made without departing from the spirit and scope of the invention.

We claim:

1. A process of preparing a biologically active urinary follicle stimulating hormone substantially free from detectable traces of luteinizing hormone and other urinary proteins which comprises subjecting a postmenopausal urinary concentrate to immunopurification using an FSH-specific immobilized monoclonal antibody, eluting said hormone using as eluent an aqueous solution having a pH higher than about 10 and anionic molarity higher than about 0.5M, removing any residual traces of contaminants by reverse phase high pressure liquid chromatography, and recovering said hormone.

2. A process according to claim 1 wherein said eluent has a pH higher than 11.

3. A process according to claim 2 wherein said eluent has an ionic molarity higher than 0.8M.

4. A process according to claim 3 wherein said eluent has a pH within the range of 11.3 to 11.7.

5. A process according to claim 4 wherein said eluent is 1M ammonia.

6. A process according to claims 1, 2, 3, 4, or 5 wherein said FSH-specific immobilized monoclonal antibody has the following specifications:
a) protein purity: not less than 90%
b) class of immunoglobulin: IgG 1
c) specificity:

| Antigen | % cross reaction |
|---|---|
| FSH | 100 |
| HCG | 1 |
| HCG-beta subunit | 1 |
| LH | 1 |
| TSH | 1 | d) binding capacity to FSH in solution: about 1,000 I.U. FSH per mg monoclonal antibody.

7. A process according to claim 6 wherein said monoclonal antibody has an affinity constant of about $3.5 \times 10^8$ L. mole$^{-1}$.

8. A process according to claim 6 wherein said hormone is recovered by use of a gradient of isopropanol up to 50% of the mobile phase in the reverse phase high pressure liquid chromatography.

9. A process according to claim 6 wherein said postmenopausal urinary concentrate is human menopausal gonadotropin.

10. A process according to claim 6 wherein said recovered hormone has a specific activity not lower than 6200 I.U. of FSH per milligram of lyophilized powder.

11. A process according to claim 6 wherein said recovered hormone is in glycosylated form.

* * * * *